(12) United States Patent
Moore, Jr. et al.

(10) Patent No.: US 6,511,682 B1
(45) Date of Patent: *Jan. 28, 2003

(54) CONCENTRATED AQUEOUS BROMINE SOLUTIONS AND THEIR PREPARATION

(75) Inventors: Robert M. Moore, Jr., Baton Rouge, LA (US); Christopher J. Nalepa, Baton Rouge, LA (US)

(73) Assignee: Albemarle Corporation, Richmond, VI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/506,911

(22) Filed: Feb. 18, 2000

Related U.S. Application Data

(63) Continuation-in-part of application No. 09/088,300, filed on Jun. 1, 1998, now Pat. No. 6,068,861, and a continuation-in-part of application No. 09/404,184, filed on Sep. 24, 1999, now Pat. No. 6,322,822.

(51) Int. Cl.$^7$ .................... A01N 39/00; A01N 59/02; A01N 59/08; A01N 59/00
(52) U.S. Cl. .................... 424/703; 424/615; 424/663; 424/665; 424/680; 424/723
(58) Field of Search ............................... 424/703, 615, 424/680, 723, 663

(56) References Cited

U.S. PATENT DOCUMENTS

| | | | |
|---|---|---|---|
| 3,152,073 A | 10/1964 | Morton | 210/62 |
| 3,170,883 A | 2/1965 | Owen et al. | 252/187 |
| 3,308,062 A | 3/1967 | Gunther | 210/58 |
| 3,328,294 A | 6/1967 | Self et al. | 210/62 |
| 3,558,503 A | 1/1971 | Goodenough et al. | 252/187 |
| 3,589,859 A | 6/1971 | Foroulis | 21/2.7 |
| 3,711,246 A | 1/1973 | Foroulis | 21/2.7 |
| 3,749,672 A | 7/1973 | Golton et al. | 252/95 |
| 3,767,586 A | 10/1973 | Rutkiewic | 252/187 H |
| 4,032,460 A | 6/1977 | Zilch et al. | 252/8.55 B |
| 4,237,090 A | 12/1980 | DeMonbrun et al. | 422/13 |
| 4,295,932 A | 10/1981 | Pocius | 162/161 |
| 4,382,799 A | 5/1983 | Davis et al. | 8/107 |
| 4,427,435 A | 1/1984 | Lorenz et al. | 71/67 |
| 4,451,376 A | 5/1984 | Sharp | 210/701 |
| 4,465,598 A | 8/1984 | Darlington et al. | 210/721 |
| 4,476,930 A | 10/1984 | Watanabe | 166/279 |
| 4,490,308 A | 12/1984 | Fong et al. | 260/513 N |
| 4,539,071 A | 9/1985 | Clifford et al. | 162/161 |
| 4,546,156 A | 10/1985 | Fong et al. | 526/240 |
| 4,566,973 A | 1/1986 | Masler, III et al. | 210/701 |
| 4,595,517 A | 6/1986 | Abadi | 252/82 |
| 4,595,691 A | 6/1986 | LaMarre et al. | 514/367 |
| 4,604,431 A | 8/1986 | Fong et al. | 525/351 |
| 4,642,194 A | 2/1987 | Johnson | 210/699 |
| 4,643,385 A | 2/1987 | Koeplin-Gall et al. | 210/754 |
| 4,661,503 A | 4/1987 | Martin et al. | 517/372 |
| 4,680,339 A | 7/1987 | Fong | 525/54.11 |
| 4,680,399 A | 7/1987 | Buchardt | 546/139 |
| 4,703,092 A | 10/1987 | Fong | 525/351 |
| 4,711,724 A | 12/1987 | Johnson | 210/699 |
| 4,752,443 A | 6/1988 | Hoots et al. | 422/13 |
| 4,759,852 A | 7/1988 | Trulear | 210/699 |
| 4,762,894 A | 8/1988 | Fong et al. | 525/344 |
| 4,777,219 A | 10/1988 | Fong | 525/329.4 |
| 4,801,388 A | 1/1989 | Fong et al. | 210/701 |
| 4,802,990 A | 2/1989 | Inskeep, Jr. | 210/699 |
| 4,822,513 A | 4/1989 | Corby | 252/106 |
| 4,846,979 A | 7/1989 | Hamilton | 210/754 |
| 4,883,600 A | 11/1989 | MacDonald et al. | 210/696 |
| 4,886,915 A | 12/1989 | Favstritsky | 564/503 |
| 4,898,686 A | 2/1990 | Johnson et al. | 252/389.2 |
| 4,906,651 A | 3/1990 | Hsu | 514/372 |
| 4,923,634 A | 5/1990 | Hoots et al. | 252/389.2 |
| 4,929,424 A | 5/1990 | Meier et al. | 422/9 |
| 4,929,425 A | 5/1990 | Hoots et al. | 422/13 |
| 4,966,716 A | 10/1990 | Favstritsky et al. | 210/755 |
| 4,992,209 A | 2/1991 | Smyk et al. | 252/387 |
| 4,995,987 A | 2/1991 | Whitekettle et al. | 210/754 |
| 5,034,155 A | 7/1991 | Soeder et al. | 252/389.23 |
| 5,035,806 A | 7/1991 | Fong et al. | 210/701 |
| 5,047,164 A | 9/1991 | Corby | 252/106 |

(List continued on next page.)

FOREIGN PATENT DOCUMENTS

| | | |
|---|---|---|
| WO | 9015780 | 12/1990 |
| WO | 9720546 | 6/1997 |
| WO | 9720909 | 6/1997 |
| WO | 9734827 | 9/1997 |
| WO | 9743392 | 11/1997 |
| WO | 9815609 | 4/1998 |
| WO | 9906320 | 2/1999 |
| WO | 9932596 | 7/1999 |
| WO | 0034186 | 6/2000 |

OTHER PUBLICATIONS

Ault et al., "Infrared and Raman Spectra of the M+Cl$_3$ –ion Pairs and Their Chlorine–bromine Counterparts isolated in Argon Matrices", Journal of Chemical Physics, 1976, vol. 64, No. 12, p. 4853–4859.

Willard et al., "Elementary Quantitative Analysis", Third Edition, Chapter XIV —Oxidation and Reduction Processes Involving Iodine (Iodometry) 1940, pp. 261–271.

*Primary Examiner*—Alton Pryor
(74) *Attorney, Agent, or Firm*—Edgar E. Spielman, Jr.

(57) ABSTRACT

Described is a process of producing a concentrated liquid biocide formulation. Mixed together are (a) bromine chloride or bromine and (b) an aqueous solution of alkali metal salt of sulfamic acid having a pH of at least about 7, in amounts such that (i) the active bromine content of the solution is at least about 100,000 ppm (wt/wt), and (ii) the atom ratio of nitrogen to active bromine from (a) and (b) is greater than 1 when bromine is used and is greater than 0.93 when bromine chloride is used. Use of bromine chloride as the source of the active bromine in the process is preferred because in the resulting aqueous compositions, all of the bromine of the bromine chloride is made available as active bromine in solution. In other words, the chlorine of the bromine chloride is converted in the process to dissolved alkali metal chloride salt, thereby liberating all of the bromine in the biocidal composition as active bromine capable of providing biocidal activity.

47 Claims, No Drawings

U.S. PATENT DOCUMENTS

| | | | |
|---|---|---|---|
| 5,055,285 A | 10/1991 | Duncan et al. | 423/473 |
| 5,118,426 A | 6/1992 | Duncan et al. | 210/721 |
| 5,120,452 A | 6/1992 | Ness et al. | 210/754 |
| 5,120,797 A | 6/1992 | Fong et al. | 525/329.4 |
| 5,141,652 A | 8/1992 | Moore, Jr. et al. | 210/754 |
| 5,179,173 A | 1/1993 | Fong et al. | 525/329.4 |
| 5,192,459 A | 3/1993 | Tell et al. | 252/106 |
| 5,194,238 A | 3/1993 | Duncan et al. | 423/473 |
| 5,196,126 A | 3/1993 | O'Dowd | 210/754 |
| 5,202,047 A | 4/1993 | Corby | 252/106 |
| 5,259,985 A | 11/1993 | Nakanishi et al. | 252/180 |
| 5,264,136 A | 11/1993 | Howarth et al. | 210/754 |
| 5,389,384 A | 2/1995 | Jooste | 424/661 |
| 5,414,652 A | 5/1995 | Mieda et al. | 365/122 |
| 5,424,032 A | 6/1995 | Christensen et al. | 422/14 |
| 5,443,849 A | 8/1995 | Corby | 424/667 |
| 5,464,636 A | 11/1995 | Hight et al. | 424/661 |
| 5,525,241 A | 6/1996 | Clavin et al. | 210/753 |
| 5,527,547 A | 6/1996 | Hight et al. | 424/661 |
| 5,589,106 A | 12/1996 | Shim et al. | 252/387 |
| 5,607,619 A | 3/1997 | Dadgar et al. | 252/187.2 |
| 5,679,239 A | 10/1997 | Blum et al. | 205/556 |
| 5,683,654 A | 11/1997 | Dallmier et al. | 422/14 |
| 5,795,487 A | 8/1998 | Dallmier et al. | 210/754 |
| 5,900,512 A | 5/1999 | Elnagar et al. | 568/14 |
| 5,922,745 A | 7/1999 | McCarthy et al. | 514/372 |
| 5,942,126 A | 8/1999 | Dallmier et al. | 210/756 |
| 6,007,726 A | 12/1999 | Yang et al. | 210/752 |
| 6,015,782 A | 1/2000 | Petri et al. | 510/379 |
| 6,037,318 A | 3/2000 | Na et al. | 510/379 |
| 6,110,387 A * | 8/2000 | Choudhury et al. | 210/752 |
| 6,123,870 A * | 9/2000 | Yang et al. | 252/186.1 |
| 6,156,229 A | 12/2000 | Yang et al. | 252/186.1 |
| 6,068,861 A1 * | 1/2001 | Moore et al. | 424/703 |
| 6,270,722 B1 | 8/2001 | Yang et al. | 422/37 |
| 6,287,473 B1 | 9/2001 | Yang et al. | 210/754 |

\* cited by examiner

CONCENTRATED AQUEOUS BROMINE SOLUTIONS AND THEIR PREPARATION

REFERENCE TO RELATED APPLICATION

This is a continuation-in-part of commonly-owned application Ser. No. 09/088,300, which continues the prosecution of commonly-owned U.S. application Ser. No. 09/088,300, filed Jun. 1, 1998, and which will be issued as U.S. Pat. No. 6,068,861, on May 30, 2000; and a continuation-in-part of commonly-owned U.S. application Ser. No. 09/404,184, filed Sep. 24, 1999, now U.S. Pat. No. 6,322,822.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to HOBr/OBr$^\ominus$. This activated solution is then introduced directly into the water system to be treated. The feeding of the two liquids in this fashion is necessary because the HOBr/OBr$^\ominus$ mixture is unstable and has to be generated on-site just prior to its introduction to the water. Furthermore, the feeding, and metering of two liquids is cumbersome, especially as the system has to be designed to allow time for the activation of bromide ion to occur. Consequently many biocide users have expressed the need for a single-feed, bromine-based biocide. Elemental bromine and molecular bromine chloride have been considered to meet these demands. Both are liquids at room temperature and can be fed directly to the water system, where immediate hydrolysis occurs to yield HOBr.

$$Br_2 + H_2O \rightarrow HOBr + HBr \quad (1)$$

$$BrCl + H_2O \rightarrow HOBr + HCl \quad (2)$$

Properties of bromine and bromine chloride are compared in Table 1.

TABLE 1

Physical Properties of Bromine and Bromine Chloride

| Property | Bromine (Br$_2$) | Bromine Chloride (BrCl) |
|---|---|---|
| Appearance | Fuming, dark-red liquid | Fuming, red liquid or gas |
| Boiling Point | 59° C. | 5° C. |
| Vapor Pressure (25° C.) | 214 mm | 1800 mm |
| Corrosivity | Corrodes most metals in the presence of water | Corrodes most metals in the presence of water |

It can be seen that certain characteristics of these materials—especially their corrosiveness, high vapor pressures and fuming tendencies—necessitate care and skill in their handling and use. Early efforts to overcome the deficiencies of these materials comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (1,3-bromochloro-5,5-dimethylhy-dantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula RSO$_3$NH$_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

THE INVENTION

This invention involves a new process of forming concentrated aqueous solutions of biocidally active bromine and in so doing, provides novel and eminently useful concentrated aqueous biocidal solutions of bromine and bromine chloride. Such concentrated solutions can be stored and shipped, and they serve as articles of commerce which, in use, are mixed into the water to be treated for microbiological control. The concentrated aqueous biocidal solutions of this invention are also useful in combating biofilms on surfaces contacted by water. Thus when put to use for microbiological control or biofilm eradication, the concentrated biocidal solutions of this invention are normally diluted in the water being treated. However, in severe cases it is possible to apply a concentrated solution of this invention directly onto a surface infested with biofilm and/or other microbial species or pathogens.

In one of its embodiments this invention provides a process of producing a concentrated liquid biocide composition which comprises mixing (a) bromine chloride or bromine with (b) an aqueous solution of alkali metal salt of sulfamic acid (preferably the sodium salt), the solution having a pH of at least about 7, e.g. in the range of about 10 to about 13.5, and preferably in the range of about 12.5 to about 13.5. The amounts of (a) and (b) used are such that (i) the content of active bromine in the concentrated solution is at least 100,000 ppm (wt/wt) and (ii) the atom ratio of nitrogen to active bromine from (a) and (b) is greater than 1 when bromine is used, and greater than 0.93 when bromine chloride is used. It is preferred that the content of active bromine in the concentrated solution is in the range of from about 145,000 ppm to about 160,000 ppm. It is also preferred, to utilize an atom ratio of nitrogen to active bromine from (a) and (b) that is greater than 1 even when using bromine chloride in the process. In a preferred embodiment the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7, e.g., in the range of 10 to about 12 or 12.5, and preferably in the range of about 12.5 to about 13.5. If sulfamic acid itself is used as the starting material, it is used initially as a slurry in water with which the alkali metal base is mixed.

When introducing the bromine chloride or bromine into the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base. When the concentrated aqueous solution is to be stored in drums, it is desirable to have the pH of such solution at about 10 or above, and preferably in the range of about 12.5 to about 13.5.

It is preferred to employ bromine chloride as the source of the active bromine in the above process because in the resulting aqueous compositions, all of the bromine of the bromine chloride is made available as active bromine capable of providing biocidal activity in solution. In other words, the chlorine of the bromine chloride is converted in the process to dissolved alkali metal chloride salt, thereby liberating the bromine as the active bromine content of the biocidal composition which is capable of providing biocidal activity. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

The term "active bromine" of course refers to all bromine-containing species that are capable of biocidal activity. It is generally accepted in the art that all of the bromine in the +1 oxidation state is biocidally active and is thus included in the term "active bromine". As is well known in the art, bromine, bromine chloride, hypobromous acid, hypobromite ion, hydrogen tribromide, tribromide ion, and organo-N-brominated compounds have bromine in the +1 oxidation state. Thus these, as well as other such species to the extent they are present, constitute the active bromine content of the compositions of this invention. See, for example, U.S. Pat. Nos. 4,382,799 and 5,679,239. A well-established method in the art for determining the amount of active bromine in a solution is starch-iodine titration, which determines all of the active bromine in a sample, regardless of what species may constitute the active bromine. The usefulness and accuracy of the classical starch-iodine method for quantitative determination of bromine and many other oxidizing agents has long been known, as witness Chapter XIV of Willard-Furman, *Elementary Quantitative Analysis,* Third Edition, D. Van Nostrand Company, Inc., New York, Copyright 1933, 1935, 1940.

A typical starch-iodine titration to determine active bromine is carried out as follows: A magnetic stirrer and 50 milliliters of glacial acetic acid are placed in an iodine flask. The sample (usually about 0.2–0.5 g) for which the active bromine is to be determined is weighed and added to the flask containing the acetic acid. Water (50 milliliters) and aqueous potassium iodide (15% (wt/wt); 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined.

By utilizing bromine or bromine chloride with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to the Goodenough, et al. patent. Moreover, even at the high levels of active bromine that exist in the compositions of this invention, it has been found possible to provide biocidal compositions that maintain these high levels of active bromine for at least a two-month period, and that do not exhibit a visible or offensive vapor or odor during this period.

In another embodiment, alkali metal dichlorohypobromite, $M[BrCl_2]$ (M=alkali metal) is preformed by pre-mixing bromine chloride with aqueous sodium chloride, and the bromine chloride is used in this form to provide the active bromine content of the resultant solution. The preferred alkali metal dichlorohypobromite is sodium dichlorohypobromite.

Another embodiment of this invention is an aqueous biocide composition comprising water having in solution therein (i) an active bromine content derived from bromine chloride of at least about 100,000 ppm (wt/wt), (ii) an alkali metal salt of sulfamic acid (preferably the sodium salt), and (iii) an alkali metal chloride (preferably sodium chloride), wherein the relative proportions of (i) and (ii) are such that the atom ratio of nitrogen to active bromine is greater than 1, and wherein the pH of the composition is at least 7, e.g., in the range of 10 to about 13.5, and preferably in the range of about 12.5 to about 13.5. It is preferred that the content of active bromine in the solution is in the range of from about 145,000 ppm to about 160,000 ppm. In a less preferred embodiment (i) is bromine ($Br_2$) and (iii) is an alkali metal bromide (especially sodium bromide).

The preferred way of forming the above aqueous biocide compositions comprising water having in solution therein an active bromine content of at least about 100,000 ppm (wt/wt), and preferably from about 145,000 ppm to about 160,000 ppm (wt/wt) is to mix together (i) bromine chloride, and (ii) an aqueous solution of alkali metal salt of sulfamic acid, or (iii) water and an alkali metal salt of sulfamic acid, or (iv) water, an alkali metal base, and sulfamic acid, or (v) any combination of (ii), (iii), and (iv), and in relative proportions of such that the atom ratio of nitrogen to active bromine in said biocide composition is greater than 0.93, preferably greater than 1, and the pH of the biocide composition is at least 7 (e.g., in the range of about 10 to about 13.5), and preferably in the range of about 12 or 12.5 to about 13.5.

This invention has made it possible to provide an aqueous biocide composition having a pH of at least 7 and that comprises water having in solution (i) an active bromine content of at least about 100,000 ppm (wt/wt), and (ii) an atom ratio of nitrogen to active bromine of greater than 0.93, the nitrogen originating from sulfamic acid and/or an alkali metal salt thereof, and in which the composition (a) is devoid or essentially devoid of bromate, and (b) since its inception has been devoid or essentially devoid of bromate. By "devoid" of bromate is meant that using the test procedure described hereinafter the level of bromate, if any, is below a detectable amount. Similarly, by "essentially devoid" ofbromate is meant that using the test procedure described hereinafter the presence of bromate is confirmed, but that the amount thereof is not more than 50 ppm (wt/wt).

In each of the embodiments of this invention, the atom ratio of nitrogen to active bromine is preferably in the range of about 1.1 to about 1.5, and more preferably in the range of from about 1.35 to about 1.5. Still higher ratios can be employed, if desired.

A further embodiment of this invention is a composition comprising an aqueous solution containing a stable oxidizing bromine compound—i.e., a stabilized active bromine content—wherein the solution is free of detectable bromate. Preferably such composition from its inception is free of detectable amounts of bromate, or in other words, the solution contains at all times from its inception less than 50 ppm of bromate. The stabilized active bromine content of the compositions of this embodiment can be derived from bromine and sulfamic acid or an alkali metal sulfamate such as sodium sulfamate or potassium sulfamate. However, most preferably the stable oxidizing bromine compound is of the type obtainable from bromine or from a combination of bromine and chlorine such as for example, bromine chloride or a mixture of bromine chloride and bromine, and sulfamic acid or an alkali metal sulfamate such as sodium sulfamate. When in the form of a concentrated solution, these compositions contain at least 100,000 ppm (wt/wt), i.e., at least 10 wt %, based on the total weight of the aqueous solution, and most preferably at least about 145,000 ppm (e.g., in the range of about 145,000 to about 160,000 ppm (wt/wt) of active bromine content. Amounts above 160,000 ppm (wt/wt) are also within the scope of this invention. In other words, any concentration of the stabilized active bromine component(s) above about 160,000 ppm (wt/wt) that does not result in precipitate formation during storage or transportation of the concentrated solution under normal ambient temperature conditions constitute compositions of this invention. When used for microbiological control, the concentrated solutions of this invention are mixed or diluted with, or introduced into, additional water, which typically is the water being treated for such microbiological control, so that the amount of active bromine in the water being treated for microbiological control is a microbiologically effective amount. The various compositions of the embodiments referred to in this paragraph preferably additionally contain dissolved chloride ion, most preferably in the presence of a stoichiometric excess of alkali metal cation, such as sodium or potassium cations. In contrast to certain other alkali metal salts, the alkali metal chloride salts have high solubilities in the aqueous medium of the concentrates of this invention, and thus pose no problem with respect to precipitate formation during storage, transportation, or use. In addition, the dissolved alkali metal chloride in the solutions of this invention minimize the extent to which oxygen or air becomes dissolved in the concentrated solutions.

Although not mandatory, it is preferred that from the inception of their production the compositions of this invention are and remain at all times free of peroxides.

Still other embodiments of this invention include the following:

1) A concentrated biocidal composition containing sulfamate-stabilized bromonium ion, such composition (i) from its inception, having a pH in excess of 8 and (ii) having greater than about 10 wt % bromonium ion present, measured as $Br_2$, such wt % being based on the total weight of the composition.

2) A concentrated biocidal composition containing sulfamate-stabilized bromonium ion, such composition (i) containing up to about 16 wt % bromonium ion, measured as $Br_2$, such wt % being based upon the total weight of the composition, (ii) from its inception, being free of detectable amounts ofbromate ion, and (iii) from its inception, having a pH greater than 10.

3) A concentrated biocidal composition containing sulfamate-stabilized bromonium ion, such composition (i) containing at least about 10 wt % bromonium ion, measured as $Br_2$, such wt % being based upon the total weight of the composition, (ii) having a pH greater than 10 and (iii) containing no detectable bromate ion.

4) A concentrated biocidal composition containing stabilized oxidizing halogen obtained by the reaction of BrCl and $^{\ominus}SO_3NH_2$, such composition (i) having up to 16 wt % bromonium ion, measured as $Br_2$, such wt % being based upon the total weight of the composition, and (ii) having a pH greater than 10.

5) A concentrated biocidal composition containing stabilized oxidizing halogen obtained by the reaction of BrCl and $^{\ominus}SO_3NH_2$, such composition having a pH greater than 10.

6) A concentrated biocidal composition containing stabilized oxidizing halogen obtained by the reaction of BrCl and $^{\ominus}SO_3NH_2$, such composition containing at least about 10 wt % bromonium ion, measured as $Br_2$, such wt % being based upon the total weight of the composition.

7) A concentrated biocidal composition containing at least about 10 wt % $^{\ominus}SO_3NH_2$ stabilized non-$BrO^{\ominus}$-oxidizing halogen.

8) A concentrated biocidal composition containing stabilized non-$BrO^{\ominus}$-oxidizing halogen, such composition having a pH greater than 10.

9) An aqueous mixture containing stabilized oxidizing halogen and having a pH between about 7 and about 8.

Preferably, but not necessarily, the composition of 1), 2), 3), 7), 8), and 9) immediately above are further characterized by comprising chloride ion in solution therein.

The above and other embodiments of this invention will be still further apparent from the ensuing description and appended claims.

A preferred alkali metal salt of sulfamic acid, and a preferred alkali metal base used in forming such salt are, respectively, potassium sulfamate and a potassium base such as KOH. Most preferred are, respectively, sodium sulfamate, and a sodium base such as NaOH.

One desirable way of accomplishing the mixing of the reactants when producing the concentrated liquid biocide formulations of this invention comprises concurrently introducing (a) bromine chloride and (b) an aqueous solution of alkali metal salt of sulfamic acid into a reaction zone, such as a reactor or other reaction vessel, and having the pH of the resulting solution at least at 7 (e.g., in the range of about 10 to about 13.5), and preferably in the range of about 12 or 12.5 to about 13.5. As noted above, the proportions of (a) and (b) used are such that (i) the active bromine content of the solution is at least about 100,000 ppm (wt/wt), preferably from about 145,000 to about 160,000 ppm (wt/wt), and (ii) the atom ratio of nitrogen to active bromine from (a) and (b) is greater than 0.93, preferably greater than 1.

A general procedure for preparing the compositions of this invention using sulfamic acid involves, as a first step, forming a slurry of sulfamic acid in water. Typically the pH of this slurry is below 1 pH unit. Sodium hydroxide at 50% concentration is then added until the solid is completely dissolved. Additional 50% NaOH is added until the desired pH is reached. Bromine or bromine chloride is then added at a rate to allow the bromine to dissolve and react with the sulfamic acid without forming a pool of halogen on the bottom of the reactor. On a laboratory scale, a convenient rate of addition is approximately two drops per second. Sodium hydroxide (e.g., 25% or 50%) is co-fed to the reactor to maintain the desired pH (e.g., in the range of 10 to about 13.5, preferably in the range of about 12 or 12.5 to about 13.5, and it may be possible to operate even at a pH in the range of 13.5 to 14. It has been found that stable solutions containing as much as 26% active bromine (11.5% on an active chlorine basis) can be prepared by the process of this invention.

One of the features of this invention is that aqueous biocide compositions are provided that, even though unpurified, are devoid or are essentially devoid of bromate. In other words, if any bromate is present, the amount thereof as determined by use of the test procedure described hereafter is such that the concentrated aqueous biocide compositions of this invention contain bromate in an amount of up to and including (i.e., no greater than) 50 ppm (wt/wt) based on the total weight of the concentrated aqueous biocidal composition. In fact, in preferred concentrated aqueous biocide compositions of this invention this bromate content is in the range of from 0 to about 40 ppm (wt/wt) as determined using such test procedure.

As is known in the art, bromate is a very undesirable component of aqueous systems. For example, U.S. Pat. No. 5,922,745 points out that in 1995 the United States Environmental Protection Agency published a paper identifying some health concerns relevant to bromate formation (G. Amy, et al., *Water Supply*, 1995, 13(1), 157), and that in the same year animal carcinogenesis was linked to the presence of low levels of bromate in drinking water (J. K. Falwell, and G. O'Neill, *Water Supply*, 1995, 13(1), 29). While some prior processing achieved reductions in the amount of bromate formed when producing stabilized aqueous bromine-containing biocides, there has remained a need for still further reductions in the amount of bromate present in such biocides. Pursuant to this invention, such further reductions have been made possible. Furthermore, because of this invention, it is now possible to form a concentrated aqueous biocide composition having an active bromine content of at least about 100,000 ppm (wt/wt), and preferably in the range of about 145,000 to about 160,000 ppm (wt/wt), which not only is devoid or essentially devoid of bromate, but which since its inception has been devoid or essentially devoid of bromate. Thus in all stages in the production, handling, storage, transportation, and use of such compositions there is a reduced possibility of exposure to bromate. So far as is known, it has not been possible to achieve such results prior to this invention. Moreover, the water treated pursuant to this invention by addition thereto of an effective biocidal amount of active bromine results in a substantial dilution since, in general, on a wt/wt basis dosages in the treated water in the range of about 0.5 to about 20 parts per million of bromine (expressed as $Br_2$) and preferably in the range of about 4 to about 10 parts per million of bromine (expressed as $Br_2$) in the aqueous medium being treated for biocidal and/or biofilm control will usually suffice. This in turn means that the very small amount of bromate, if any, present in the concentrated aqueous solution of this invention is sharply reduced by orders of magnitude in the water being treated while achieving the microbiological control for which the composition is being used.

Still another feature of this invention is that the invention has made it possible to form a concentrated aqueous biocide composition having an active bromine content of at least about 100,000 ppm (wt/wt), which not only is devoid or essentially devoid of bromate, but which, since its inception, has always had a pH of greater than 8, and preferably in the range of about 12 to about 13.5. Thus it is not necessary to first reduce pH during processing and thereafter to increase the pH of the product solution. Avoidance of such pH adjustments materially simplifies the operations involved in the production of the resultant concentrated aqueous biocide composition of this invention. In addition, when the composition has been maintained at a pH of at least 12 or 13, e.g., in the range of 12 to about 13.5, from its inception, the possibility of bromate formation caused by exposure of the composition to reduced pH is virtually eliminated.

A further advantage of this invention is that it is unnecessary to produce the concentrated aqueous biocide compositions of this invention by use of powerful oxidants such as ozone or peroxides, which are known to possess undesirable, and indeed, hazardous characteristics.

The analytical test procedure to be used for determining the concentration, if any, of bromate in the compositions of this invention is an ion chromatography procedure in which UV detection is employed. The equipment required for the conduct of this procedure is as follows:
 a) Ion Chromatograph—Dionex DX-500 or equivalent, equipped with a UV detector and autosampler.
 b) Data Acquisition and Analysis Device—VAX MULTICHROM or equivalent chromatography data collection and processing system.
 c) Ion Chromatographic Column—Dionex IonPac AG9-HC guard column (p/n 051791) in-line with a Dionex IonPac AS9-HC column (p/n 051786).
 d) Volumetric Pipettes—any standard type of suitable volume.
 e) Autosampler Vials—1-mL with caps.
 f) Volumetric Flasks—100-mL.
 g) Syringe—5-cc plastic syringe.
 h) Pretreatment Cartridge—OnGuard-H from Dionex (p/n 039596).

The chemicals required for use in the procedure are as follows:
 a) Water—Deionized water with a specific resistivity of 17.8 megohm-cm or greater.
 b) Sodium Carbonate—"Baker Analyzed"® reagent grade or equivalent.
 c) Sodium Bromate—"Baker Analyzed"® reagent grade or equivalent.

The conditions used for the ion chromatograph are as follows:

| Eluent: | 4.5 millimoles (mM) sodium carbonate |
|---|---|
| Flow-rate | 1.0 mL/minute |
| Injection volume | 50 microliter ($\mu$L) |
| Detector Range | UV at 210 nanometers (nm) |

The eluent is prepared by dissolving 0.4770 gram of the sodium carbonate in 1 liter of the deionized water. These are mixed well and the solution is filtered through a 0.2 IC compatible filter to degas the solution. The concentrated bromate standard solution is prepared by weighing 0.1180 gram±0.001 gram of the sodium bromate into a 100-mL volumetric flask and diluting to volume with deionized water. This produces a solution containing 1,000 micrograms per milliliter of bromate. This concentrated bromate solution should be made fresh at least weekly. The bromate working standard solution is prepared by pipetting 100-microliters of the concentrated bromate standard solution into a 100-mL volumetric flask and filling the flask to volume with deionized water. The solution is mixed well, and yields a standard concentration of 1.0 microgram per milliliter of bromate.

The detailed procedure used for conducting the analysis of an aqueous solution of this invention involves the following steps:
 a) Weigh 0.25 gram of the sample solution into a 100-mL volumetric flask. Fill to volume with deionized water and mix well.
 b) Flush the OnGuard cartridge with 2-mL of deionized water.
 c) Load 5-mL of the sample into the syringe attached to the OnGuard cartridge, pass through at a flow rate of 2 milliliters per minute, and discard the first 3 milliliters. Collect into a 1-mL autosampler vial and cap for analysis.
 d) Analyze the samples, making duplicate injections, using the Ion Chromatograph instrument conditions given above.

The calculations involved in the procedure are as follows:
 a) Calibration Standard: For bromate, calculate a response factor as follows: R=A/C where R is the response factor, A is the average area counts (2 injections), and C is concentration in micrograms per milliliter ($\mu$g/mL).
 b) Samples: ppm bromate=A/(R×W) where A is the average area of sample peak (2 injections), R is the response factor, and W is the weight of the sample in grams.

The following examples are presented for purposes of illustration and not limitation.

EXAMPLES

Various compositions were prepared using the above general procedure and the active bromine content of the resultant compositions was determined analytically. The conditions used results obtained (observations on odor and vapor, and initial contents of active bromine in the solutions) are summarized in Table 2.

TABLE 2

Data on Prepared Sulfamic Acid Stabilized Bromine Solutions

| Ex. No. | Halogen | pH | SA$_{eq}$ | Odor and Vapor Comments | Active Bromine, wt % |
|---|---|---|---|---|---|
| 1 | Br$_2$ | 13.0 | 1.42 | Slight sweet smell, no observed vapor | 12.4%* |
| 2 | Br$_2$ | 7.0 | 1.48 | Slight Br odor, no fuming | 13.4%* |
| 3** | BrCl | 7 | 0.92 | Strong Br odor, slight fuming | 11.2% |
| 4 | Br$_2$ | 13.0 | 1.15 | Slight sweet smell, no observed vapor | 19.6% |
| 5 | Br$_2$ | 7.0 | 1.13 | Moderate Br odor, no fuming | 26.7% |
| 6 | BrCl | 12.5 | 0.94 | Slight sweet smell, no observed vapor | 18.0% |
| 7 | BrCl | 12.8 | 1.41 | Slight sweet smell, no observed vapor | 17.6% |

SA$_{eq}$ = Sulfamic acid to halogen mole ratio.
*Measured with Hach spectrometer; all others titrated using starch-iodine-sodium arsenite method.
**Comparative example.

The specific details for Examples 3–7 of the Table are given below. Example 8 illustrates the embodiment of the invention wherein an alkali metal dichlorohypobromite is utilized as the source of active bromine.

Example 3

Bromine Chloride, Caustic and Sodium Sulfamate at Neutral pH

A 1 liter flask was charged with 52.0 g of sulfamic acid and 250 g of water. Sodium sulfamate was prepared by adding 60.0 g of 50% sodium hydroxide to the stirred slurry. Bromine chloride was prepared by adding 20 g of chlorine to 47.0 g of bromine. This bromine chloride was then co-fed with 210 g of 25% sodium hydroxide to maintain the pH between 6 and 8. 5 mL of 1 M Hydrochloric Acid were added to bring the final pH to approximately 7±0.5. The solution, which contained some solids, was transferred to an amber bottle for storage. Starch-iodine titration of a sample of the solution indicated that it had an active bromine concentration of 11.2%.

Example 4
Bromine, Caustic (50% Sodium Hydroxide) and Sodium Sulfamate

A 500 mL flask was charged with 26.0 g of sulfamic acid and 50 g water. To this slurry was added 35.0 g of 50% sodium hydroxide. As the acid was converted to the sodium salt, it dissolved into the aqueous solution more readily. Bromine (37.0 g) and 50% sodium hydroxide (30.0 g) were co-fed into the solution at a rate which maintained the pH between 11 and 13. After all of the bromine and caustic had been added, the contents were transferred to an amber bottle for storage. Starch-iodine titration of a sample of the solution indicated that it had an active bromine concentration of 19.6%. Analysis of the bromine solution still contained more than 95% of its active bromine content.

Example 5
Bromine, Caustic and Sodium Sulfamate at Neutral pH

A 500 mL flask was charged with 26.0 g of sulfamic acid and 50 g of water. To this stirred slurry was added 30.9 g of 50% sodium hydroxide, which raised the initial pH to approximately 12. The sulfamic acid then dissolved into solution. Bromine (37.7 g) was fed into the solution until the pH dropped to approximately 7, when 50% sodium hydroxide (10.9 g) was co-fed to maintain the pH between 6 and 9. 5 mL of 0.01 N sodium hydroxide was used to bring the final pH to approximately 7±0.5. The contents were then transferred to an amber bottle for storage. Starch-iodine titration of a sample of this solution indicated that it had an active bromine content of 26.7%. Analysis of the solution after six weeks of storage at ambient temperature indicated that the stabilized bromine solution still contained more than 95% of its active bromine content.

Example 6
Bromine Chloride, Caustic and Sodium Sulfamate

A 1 liter flask was charged with 107 g of sulfamic acid and 200 g of water. Sodium sulfamate was prepared by adding 93.9 g of 50% sodium hydroxide to the stirred slurry. Bromine chloride was prepared by adding 39 g of chlorine to 96.0 g of bromine. This bromine chloride was the co-fed with 319 g of 50% sodium hydroxide to maintain the pH between 11 and 13. After stirring for an additional 30 minutes, the solution, which contained some solids, was transferred to an amber bottle for storage. Starch-iodine titration of a sample of the solution indicated that it had an active bromine concentration of 18.0%. Analysis of the solution after three weeks at ambient temperature indicated that the stabilized bromine solution still contained more than 90% of its active bromine content.

Example 7
Bromine Chloride, Caustic and Sodium Sulfamate; Larger Scale

A 5 liter flask was charged with 470 g of sulfamic acid and 900 g of water. Sodium sulfamate was prepared by adding 436 g of 50% sodium hydroxide to the stirred slurry. Bromine chloride was prepared by adding 120 g of chlorine to 276 g of bromine. This bromine chloride was the co-fed with 1723 g of 50% sodium hydroxide to maintain the pH between 12 and 13. After stirring for an additional 60 minutes, the orange, clear solution was transferred to an polyethylene bottle for storage. Starch-iodine titration of a sample of the solution indicated that it had an active bromine concentration of 17.6%.

Example 8
Bromine Chloride, Caustic and Sodium Sulfamate; Larger Scale

A 5 liter flask was charged with 390 g of sulfamic acid and 400 g of water. Sodium sulfamate was prepared by adding 1820 g of 25% sodium hydroxide to the stirred slurry while cooling to keep the temperature below 30° C. 344 g of bromine chloride was then added. The orange, clear solution had a pH of 13.5, and was filtered and transferred to a polyethylene bottle for storage. Starch-iodine titration of a sample of the solution indicated that it had an active bromine concentration of 16.2%.

Example 9
Reducing Vapor Pressure of Sodium Dichlorohypobromite with Sodium Sulfamate Sodium sulfamate was prepared by slurrying 24.3 g of sulfamic acid in 9 g of water. 24.0 g of 50% sodium hydroxide was added dropwise. The flask heated noticeably and the solid dissolved. This solution was dropped into 184.6 g of sodium dichlorohypobromite. Sodium dichlorohypobromite, $Na[BrCl_2]$ is prepared by adding 30.6 g of bromine chloride to 154 g of 3M aqueous sodium chloride. An additional 24 g of 50% sodium hydroxide was added to raise the pH to 7. Analysis of this solution indicated that it had an active bromine concentration of 12.0%.

At present, a preferred way of conducting the process of this invention on a larger scale involves charging to a reactor water, aqueous alkali metal hydroxide solution (preferably aqueous sodium hydroxide solution), sulfamic acid, and then bromine chloride or a mixture of bromine chloride and bromine. Preferred proportions of the components are 17 parts by weight of water, 59 parts by weight of a 25 wt % aqueous sodium hydroxide solution, 13 parts by weight of sulfamic acid, and 11 parts by weight of bromine chloride, for a total of 100 parts by weight. Preferably these components are charged in the order named. However, as long as the bromine chloride is charged last, the order of addition of the other three components can be varied. The bromine chloride used preferably contains in the range of 68.9 to 73.1 wt % bromine. However, pure bromine chloride or other combinations of bromine chloride and bromine can be used to make effective product, if desired. The temperature of the mixture during the addition of the bromine chloride is preferably not allowed to exceed 50° C., although the temperature can be allowed to go above 50° C. for short periods of time without detrimental effects. Prolonged exposure to elevated temperatures tends to cause degradation of the product, and thus should be avoided. The bromine chloride concentration in the resultant product solution as formed in this manner (and in whatever chemical form or forms the active bromine chloride exists in such solution), is between 14.5 and 16.0 wt % (i.e., between 145,000 and 160,000 ppm (wt/wt)), and preferably is targeted at about 15.0 wt % (i.e., at about 150,000 ppm (wt/wt)). Determination of such concentration can, of course, be readily accomplished by starch-iodine titration. When operating as described in this paragraph, the final pH of the product solution is in the range of about 12.4 to about 13.7. It will be understood and appreciation that pursuant to this invention an equivalent amount of bromine can be used in this processing in lieu of bromine chloride or mixtures of bromine chloride and bromine.

Another preferred way of operating on a larger scale the process described in the immediately preceding paragraph is in a semi-continuous or semi-batch mode. This involves forming the alkali metal sulfamate solution, preferably a sodium sulfamate solution (using caustic, water, sulfamic acid), and feeding in the bromine chloride or bromine chloride and bromine (BrCl) to a suitable vessel (reactor, tank, etc.) containing the sulfamate solution. The BrCl may go straight into the vessel of the aqueous sodium sulfamate or into a pumparound loop on the vessel. The BrCl may be made up ahead of time, or can be made by continuously mixing the bromine and chlorine together in a pipe, with or without a mixing element, and then injecting it straight into the aqueous sodium sulfamate without isolating the BrCl. The advantage of continuously making the BrCl is that this avoids having a separate BrCl reactor or storage tank and the need for keeping a large quantity of this material in storage on plant facilities.

Besides being useful in the microbiocidal treatment of aqueous media such as recreational water, industrial cooling water, process water, and wastewater, the concentrated solutions of this invention can be used for eradicating, or at least reducing, biofilm on surfaces contacted by aqueous media such as cooling tower surfaces, filter surfaces, surfaces in pools and spas, interior surfaces of pipes and conduits, and similar surfaces on which biofilm can develop. Besides causing damage and/or unsightliness to the surfaces to which the bacterial films become tenaciously attached, biofilms can harbor dangerous pathogens. And because they can form slime layers, biofilms can interfere with normal water flow. Despite the fact that the slimy films themselves constitute protective barriers against penetration of biocidal agents, the biocidal solutions of this invention enable effective biocidal control of biofilms. Thus pursuant to this invention the concentrated aqueous solutions of this invention can be used for introducing biocidally effective amounts of active bromine into aqueous systems that come into contact with surfaces infested with biofilm and thereby at least reduce the biofilm, if not eradicate the biofilm in its entirety. This is of course accomplished by adding an amount of a concentrated aqueous solution of this invention to the water to be treated for biofilm reduction or eradication, the amount of such addition being an amount (dosage) that will at least reduce the biofilm, if not eradicate the biofilm in its entirety. Generally speaking, dosages in the range of about 0.5 to about 20 parts per million of active bromine (expressed as $Br_2$) and preferably in the range of about 4 to about 10 parts per million of active bromine (expressed as $Br_2$) in the aqueous medium being treated for biofilm control will usually suffice, but lesser or greater amounts of active bromine can be used whenever deemed necessary, appropriate, or desirable. Naturally there may be some period of time that will pass between the time that the concentrated aqueous solution of this invention is brought into contact with, and thus diluted in, the water being treated, and the time that the biofilm is reduced or eradicated. If desired, such reduction or eradication can be observed by periodically visually inspecting the water-contacted surfaces that are infested with the biofilm, assuming such surfaces are in a location that one can observe. In the case of filters, conduits, or pipes infested with biofilm and carrying water treated pursuant to this invention with a biocidal amount (dosage) of a concentrated aqueous solution of this invention to reduce or eradicate such biofilm, the reduction or eradication of biofilm may be evidenced and thus observed by improved performance of the apparatus (e.g., increased water flow). But whether or not such observations are made, when a biocidally effective amount of active bromine is included in the water that comes in contact with the biofilm after addition to such water of a suitable dosage of a concentrated solution of this invention, reduction or eradication of the biofilm will occur.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing a concentrated liquid biocide formulation which comprises introducing (a) bromine chloride into (b) an aqueous solution of alkali metal salt of sulfamic acid, and having the pH of the resulting solution at least at about 10 using an alkali metal base, the proportions of (a) and (b) used being such that (i) the active bromine content of the solution is at least about 100,000 ppm (wt/wt), and (ii) the atom ratio of nitrogen to active bromine from (a) and (b) is greater than 0.93.

2. A process according to claim 1 wherein said atom ratio is greater than 1.

3. A process according to claim 1 wherein said pH is in the range of about 12.5 to about 13.5.

4. A process according to claim 1 wherein said atom ratio is greater than 1, and wherein said pH is in the range of about 12.5 to about 13.5.

5. A process according to claim 1 wherein the bromine chloride being introduced into the aqueous solution of (b) has a bromine content in the range of about 68.9 to about 73.1 wt %.

6. A process according to claim 1 wherein said atom ratio is greater than 1, and wherein the bromine chloride being introduced into the aqueous solution of (b) has a bromine content in the range of about 68.9 to about 73.1 wt %.

7. A process according to claim 1 wherein said pH is in the range of about 12.5 to about 13.5, and wherein the bromine chloride being introduced into the aqueous solution of (b) has a bromine content in the range of about 68.9 to about 73.1 wt %.

8. A process according to claim 1 wherein said atom ratio is greater than 1, wherein said pH is in the range of about 12.5 to about 13.5, and wherein the bromine chloride being introduced into the aqueous solution of (b) has a bromine content in the range of about 68.9 to about 73.1 wt %.

9. A process according to claim 1 wherein said aqueous solution of alkali metal salt of sulfamic acid is an aqueous solution of the sodium salt of sulfamic acid.

10. A process according to claim 9 wherein said atom ratio is greater than 1.

11. A process according to claim 9 wherein said pH is in the range of about 12.5 to about 13.5.

12. A process according to claim 9 wherein said atom ratio is greater than 1, and wherein said pH is in the range of about 12.5 to about 13.5.

13. A process according to claim 9 wherein the bromine chloride being introduced into the aqueous solution of (b) has a bromine content in the range of about 68.9 to about 73.1 wt %.

14. A process according to claim 9 wherein said atom ratio is greater than 1, and wherein the bromine chloride being introduced into the aqueous solution of (b) has a bromine content in the range of about 68.9 to about 73.1 wt %.

15. A process according to claim 9 wherein said pH is in the range of about 12.5 to about 13.5, and wherein the bromine chloride being introduced into the aqueous solution of (b) has a bromine content in the range of about 68.9 to about 73.1 wt %.

16. A process according to claim 9 wherein said atom ratio is greater than 1, wherein said pH is in the range of about 12.5 to about 13.5, and wherein the bromine chloride being introduced into the aqueous solution of (b) has a bromine content in the range of about 68.9 to about 73.1 wt %.

17. A process according to claim 1 wherein said aqueous solution of alkali metal salt of sulfamic acid is formed by mixing together in water, (1) sulfamic acid and/or an alkali metal salt of sulfamic acid, and (2) alkali metal base in proportions such that an aqueous solution of alkali metal salt of sulfamic acid is formed having a pH of at least 10.

18. A process according to claim 17 wherein said atom ratio is greater than 1.

19. A process according to claim 17 wherein said pH is in the range of about 12.5 to about 13.5.

20. A process according to claim 19 wherein the bromine chloride being introduced into the aqueous solution of (b) has a bromine content in the range of about 68.9 to about 73.1 wt %.

21. A process according to claim 17 wherein said atom ratio is greater than 1, and wherein said pH is in the range of about 12.5 to about 13.5.

22. A process according to claim 21 wherein the bromine chloride being introduced into the aqueous solution of (b) has a bromine content in the range of about 68.9 to about 73.1 wt %.

23. A process according to claim 17 wherein said alkali metal base is a sodium base such that said aqueous solution of alkali metal salt of sulfamic acid is an aqueous solution of sodium salt of sulfamic acid.

24. A process according to claim 23 wherein said atom ratio is greater than 1.

25. A process according to claim 23 wherein said pH is in the range of about 12.5 to about 13.5.

26. A process according to claim 23 wherein said atom ratio is greater than 1, and wherein said pH is in the range of about 12.5 to about 13.5.

27. A process according to claim 17 wherein, at the time (1) and (2) are mixed together, the alkali metal base is in the form of a preformed aqueous solution of alkali metal base, and (2) is sulfamic acid in the form of a preformed slurry of sulfamic acid in water.

28. A process according to claim 27 wherein said atom ratio is greater than 1.

29. A process according to claim 27 wherein said preformed aqueous solution of alkali metal base is a preformed aqueous solution of sodium base.

30. A process according to claim 29 wherein the bromine chloride being introduced into the aqueous solution of (b) has a bromine content in the range of about 68.9 to about 73.1 wt %.

31. A process according to claim 29 wherein said atom ratio is greater than 1, wherein said pH is in the range of about 12.5 to about 13.5.

32. A process according to claim 31 wherein the bromine chloride being introduced into the aqueous solution of (b) has a bromine content in the range of about 68.9 to about 73.1 wt %.

33. A process according to claim 1 wherein said aqueous solution of alkali metal salt of sulfamic acid is an aqueous solution of the potassium salt of sulfamic acid.

34. A process according to any of claims 1–33 wherein the active bromine content of the solution is in the range of about 145,000 ppm (wt/wt) to about 160,000 ppm (wt/wt).

35. A process of producing a concentrated liquid biocide formulation which comprises:

A) mixing together sulfamic acid and a preformed, at least 25 wt % aqueous sodium hydroxide solution, in proportions such that an aqueous solution of sodium salt of sulfamic acid is formed having a pH of at least about 10; and B) introducing bromine chloride into said aqueous solution in an amount such that (i) the active bromine content of the resulting solution is at least about 100,000 ppm (wt/wt), and (ii) the atom ratio of nitrogen to active bromine is greater than 0.93 and wherein the sodium hydroxide used is such that the resulting solution has a pH of at least about 10.

36. A process according to claim 35 wherein before said mixing in A), the sulfamic acid is mixed with water to form an aqueous slurry of sulfamic acid, and said preformed aqueous sodium hydroxide solution is added to said slurry.

37. A process according to claim 35 wherein said pH is in the range of from about 10 to about 13.5.

38. A process according to claim 35 wherein said pH is in the range of from about 12 to about 13.5.

39. A process according to claim 35 wherein the bromine chloride being introduced into the aqueous solution of B) has a bromine content in the range of about 68.9 to about 73.1 wt %.

40. A process according to claim 35 wherein said atom ratio is greater than 1.

41. A process according to claim 40 wherein the bromine chloride being introduced into the aqueous solution of B) has a bromine content in the range of about 68.9 to about 73.1 wt %.

42. A process according to any of claims 35–41 wherein the active bromine content of the solution is in the range of about 145,000 ppm (wt/wt) to about 160,000 ppm (wt/wt).

43. A process of producing a concentrated liquid biocide formulation which comprises concurrently introducing (a) bromine chloride and (b) an aqueous solution of alkali metal salt of sulfamic acid into a reaction zone, and having the pH of the resulting solution at least 7 using an alkali metal base, the proportions of (a) and (b) used being such that (i) the active bromine content of the resulting solution is at least about 100,000 ppm (wt/wt), and (ii) the atom ratio of nitrogen to active bromine from (a) and (b) is greater than 0.93.

44. A process according to claim 43 wherein said pH is in the range of from 7 to about 13.5, and wherein said atom ratio is greater than 1.

45. A process according to claim 44 wherein said pH is in the range of from about 12 to about 13.5.

46. A process according to claim 44 wherein the bromine chloride of (a) has a bromine content in the range of about 68.9 to about 73.1 wt %.

47. A process according to any of claims 44–46 wherein the active bromine content of the solution is in the range of about 145,000 ppm (wt/wt) to about 160,000 ppm (wt/wt).

* * * * *